(12) United States Patent
Ausubel et al.

(10) Patent No.: US 6,794,133 B1
(45) Date of Patent: Sep. 21, 2004

(54) BROAD RANGE PCR AMPLIFICATION TECHNIQUES

(75) Inventors: Frederick M. Ausubel, Newton, MA (US); Michael Mindrinos, Menlo Park, CA (US); Eliana Drenkard, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/581,106

(22) PCT Filed: Dec. 3, 1998

(86) PCT No.: PCT/US98/25665

§ 371 (c)(1),
(2), (4) Date: Jan. 30, 2001

(87) PCT Pub. No.: WO99/29901

PCT Pub. Date: Jun. 17, 1999

Related U.S. Application Data

(60) Provisional application No. 60/069,230, filed on Dec. 11, 1997.

(51) Int. Cl.$^7$ .............................. C12Q 1/68; C12Q 1/70; C12P 19/34; C07H 21/04

(52) U.S. Cl. ........................ 435/6; 435/91.2; 435/91.1; 435/5; 536/24.33; 935/77; 935/78

(58) Field of Search .......................... 435/6, 91.2, 91.1, 435/5; 536/24.33; 935/77, 78

(56) References Cited

U.S. PATENT DOCUMENTS

| | | | |
|---|---|---|---|
| 4,965,188 A | * 10/1990 | Mullis et al. | .................... 435/6 |
| 5,143,854 A | 9/1992 | Pirrung et al. | .............. 436/518 |
| 5,496,699 A | 3/1996 | Sorenson | ........................ 435/6 |
| 5,595,890 A | * 1/1997 | Newton et al. | ............. 435/91.2 |

FOREIGN PATENT DOCUMENTS

| | | | | |
|---|---|---|---|---|
| EP | 0 332 435 B2 | 10/1999 | ............ | C12Q/1/68 |
| WO | WO 92/10092 | 6/1992 | ............ | A01N/1/02 |

OTHER PUBLICATIONS

Cha et al., "Mismatch Amplification Mutation Assay (MAMA): Application to the c–H–ras Gene" *PCR Methods and Applications* 2:14–20 (1992).
Chang et al., "Multiplex Mutagenically Separated PCR: Diagnosis of the β–Thalassemia and Hemoglobin Variants" *BioTechniques* 22:520–527 (1997).
Chee et al., "Accessing Genetic Information with HighDensity DNA Arrays" *Science* 274:610–614 (1996).
Cheng et al., Chip PCR. II. Investigation of Different PCR Amplification Systems in Microfabricated Silicon–Glass Chips *Nucleic Acids Research* 24:380–385 (1996).
Devos et al., "The Use of Random Amplified Polymorphic DNA Markers in Wheat" *Theor. Appl. Genet.* 84:567–572 (1992).
Dietrich et al., "A Genetic Map of the Mouse Suitable for Typing Intraspecific Crosses" *Genetics* 131:423–447 (1992).
Dietrich et al., "Mapping the Mouse Genome: Current Status and Future Prospects" *Proc. Natl. Acad. Sci. USA*, 92:10849–10853 (1995).
Ferrie et al., "Development, Multiplexing, and Application of ARMS Tests for Common Mutations in the CFTR Gene" *Am. J. Human Genetics* 51:251–262 (1992).
Fodor et al., "Light–Directed, Spatially Addressable Parallel Chemical Synthesis" *Science* 251:767–773 (1991).
Guyer et al., "How is the Human Genome Project Doing, and What Have We Learned So Far" *Proc. Natl. Acad. Sci. USA* 92:10841–10848 (1995).
Huang et al., "Extension of Base Mispairs by TAQ DNA Polymerase: Implications for Single Nucleotide Discrimination in PCR" *Nucleid Acids Research* 20:4567–4573 (1992).
Kwok et al., "A Guide to the Design & Use of Mismatched and Degenerate Primers" *PCR Methods and Applications; Manual Supplement* S39–S47 (1994).
Kwok et al., "Effects of Primer–template Mismatches on the Polymerase Chain Reaction: Human Immunodeficiency Virus Type 1 Model Studies" *Nucleic Acids Research* 18:999–1005 (1990).
Li et al., "Direct Electrophoretic Detection of the Alielic State of Single DNA Molecules in Human Sperm by Using the Polymerase Chain Reaction" *Proc. Natl. Acad. Sci USA* 87:4580–4584 (1990).
Lipshutz et al., "Using Oligonucleotide Probe Arrays To Access Genetic Diversity" *BioTechniques* 19:442–447 (1995).
Newton et al., "Analysis of any Point Mutation in DNA. The Amplification Refractory Mutation System (ARMS)" *Nucleic Acids Research* 27:2503–2516 (1989).
Pease et al., "Light–Generated Oligonucleotide Arrays for Rapid DNA Sequence Analysis" *Proc. Natl. Acad. Sci. USA* 91:5022–5026 (1994).
Riedy et al., "Excess of Non–Parental Bands in Offspring from Known Primate Pedigrees Assayed Using RAPD PCR" *Nucleic Acids Research* 20:918 (1992).

(List continued on next page.)

*Primary Examiner*—Kenneth R. Horlick
*Assistant Examiner*—Joyce Tung
(74) *Attorney, Agent, or Firm*—Clark & Elbing LLP

(57) ABSTRACT

Disclosed herein are methods and kits for determining whether a nucleic acid sequence includes a particular allele of a polymorphic sequence. These methods and kits focus on two sets of primers that are specific for an allele and are contacted with a nucleic acid sequence. One primer in each set is complementary to the polymorphic sequence at its 3'-terminal nucleotide and contains one or more mismatches in the five nucleotide adjacent to the 3' terminus. The two sets of primers preferentially amplify methods are used to identify single nucleotide polymorphisms, for example, for genomic mapping purpose.

18 Claims, 6 Drawing Sheets

OTHER PUBLICATIONS

Schena et al., "Parallel Human Genome Analysis: Microarray–Based Expression Monitoring of 1000 Genes" *Proc. Natl. Acad. Sci. USA* 93:10614–10619 (1996).

Schena et al., "Quantitative Monitoring of Gene Expression Patterns with a Complementary DNA Micorarray" *Science* 270:467–470 (1995).

Southern, "DNA Chips: Analysing Sequence by Hybridization to Oligonucleotides on a Large Scale" *Trends in Genetics* 12:110–115 (1996).

Sommer et al., "PCR Amplification of Specific Alleles (PASA) is a General Method for Rapidly Detecting Know Single–Base Changes" *BioTechniques* 12:82–87 (1992).

Ugozzoli et al., "Allele–Specific Polymerase Chain Reaction" *METHODS: A Companion to Methods in Enzymology* 2:42–48 (1991).

Vos et al., "AFLP: A New Technique for DNA Fingerprinting" *Nucleic Acids Research* 23:4407–4414 (1995).

Wenham et al., "Analysis of Apolipoprotein E Genotypes by the Amplification Refractory Mutation System" *Clinical Chemistry* 37:241–244 (1991).

Williams, et al., "DNA Polymorphisms Amplified by Arbitrary Primers are Useful as Genetic Markers" *Nucleic Acids Research* 18: 6531–6535 (1990).

Jordan et al., "A March of Genetic Maps" *Nature* 380:111–112 (1996).

Kozal et al., "Extensive Polymorphisms Observed in HIV–1 Clade B Protease Gene Using High–Density Oligonucleotide Arrays" *Nature Medicine* 2:753–759 (1996).

Lo et al., "Direct Haplotype Determination by Double ARMS: Specificity, Sensitivity and Genetic Applications" *Nucleic Acids Research* 19:3561–3567 (1991).

Petruska et al., "Comparison Between DNA Melting Thermodynamics and DNA Polymerase Fidelity" *Proc. Natl. Acad. Sci. USA*, 85:6252–6256 (1998).

Sarkar et al., "Characterization of Polymerase Chain Reaction Amplification of Specific Alleles" *Analytical Biochemistry* 186:64–68 (1990).

* cited by examiner 0.01 nanograms of template DNA

|         | P1 | P2 | P3 | P4 |
|---------|----|----|----|----|
| Allele A | + | + | − | − |
| Allele B | − | − | + | − |

0.1 nanograms of template DNA

|         | P1 | P2 | P3 | P4 |
|---------|----|----|----|----|
| Allele A | + | + | − | − |
| Allele B | − | − | + | + |

10 nanograms of template DNA

|         | P1 | P2 | P3 | P4 |
|---------|----|----|----|----|
| Allele A | + | + | + | − |
| Allele B | − | − | + | + |

BROAD RANGE PCR AMPLIFICATION TECHNIQUES

CROSS-REFERENCE TO RELATED APPLICATIONS

This application is the National Stage of International Application No. PCT/US98/25665, filed on Dec. 3, 1998, which claims benefit of U.S. Provisional Application No. 60/069,230, filed Dec. 11, 1997, now abandoned.

STATEMENT AS TO FEDERALLY SPONSORED RESEARCH

This invention was made with Government support from the National Science Foundation under Grant No. MCB 9405961. The Government has certain rights in the invention.

BACKGROUND OF THE INVENTION

The invention relates to novel polymerase chain reaction (PCR) amplification techniques and their use, for example, for identifying single nucleotide polymorphisms.

Dense linkage maps are invaluable tools for genetic and genomic analysis. They facilitate high resolution genetic mapping, positional cloning of monogenic traits, genetic dissection of polygenic traits, fine-structure linkage disequilibrium studies, and the construction of genome-wide physical maps. Historically, genetic maps were constructed with visible markers, but it is difficult to examine many such markers in a single cross. The recognition that distantly related individuals differ in DNA sequence throughout their genome (Botstein et al., Am. J. Hum. Genet. 32: 314–331, 1980) led to the rapid incorporation of DNA markers into mapping strategies. Useful DNA markers have the following general characteristics: (1) they are inherited in a Mendelian fashion; (2) they are present in most individuals analyzed and recognize a sequence that is polymorphic; (3) they correspond to a single site in the genome; (4) the probe used to recognize the marker hybridizes selectively and efficiently, even under conditions of low stringency; and (5) they can be distributed throughout a community, either as clones or as DNA sequences.

Until recently, the most commonly used DNA markers were restriction fragment length polymorphisms (RFLPs), anonymous single copy-number genomic clones that reveal a polymorphism in the length of a restriction fragment, typically by DNA blot hybridization. RFLP mapping is well-suited for determining the genetic location of any newly-cloned DNA sequence; the DNA fragment can be used as a hybridization probe (assuming it detects an RFLP) against the DNA filters used to construct the RFLP map. However, in many cases, new genes are identified by mutations, and mapping such a mutation onto an RFLP map can be a lengthy and arduous procedure.

SUMMARY OF THE INVENTION

In general, the invention features a method for determining whether a nucleic acid sequence includes a particular allele of a polymorphic sequence, involving:

(a) contacting a nucleic acid sequence, in the same or a separate reaction, with a first pair of PCR primers and a second pair of PCR primers under conditions that allow hybridization of the PCR primers to the nucleic acid sequence, the first pair of PCR primers hybridizing to opposite strands of the nucleic acid sequence and bordering the position of the polymorphic sequence, and the second pair of PCR primers hybridizing to opposite strands of the nucleic acid sequence and bordering the position of the polymorphic sequence, the PCR primers being characterized as follows:
  (i) one of the first pair of PCR primers (a) being complementary at its 3'-terminal nucleotide to a first allele of the polymorphic sequence (allele A), (b) being non-complementary at its 3'-terminal nucleotide to a second allele of the polymorphic sequence (allele B), and (c) being non-complementary to the nucleic acid sequence at a single non-complementary nucleotide in its 3'-terminal nucleotides 2–6; and
  (ii) one of the second pair of PCR primers (a) being complementary at its 3'-terminal nucleotide to the first allele of the polymorphic sequence (allele A), (b) being non-complementary at its 3'-terminal nucleotide to the second allele of the polymorphic sequence (allele B), and (c) being non-complementary to the nucleic acid sequence at one (and, preferably, two) or more nucleotides in its 3'-terminal nucleotides 2–6;

(b) carrying out the amplification reactions; and (c) detecting an amplification product as an indication of the presence, in the nucleic acid sequence, of the first allele of the polymorphic sequence (allele A).

If desired, the method may involve the further steps of:

(a) contacting the nucleic acid sequence, in the same or a separate reaction, with a third pair of PCR primers and a fourth pair of PCR primers under conditions that allow hybridization of the PCR primers to the nucleic acid sequence, the third pair of PCR primers hybridizing to opposite strands of the nucleic acid sequence and bordering the position of the polymorphic sequence, and the fourth pair of PCR primers hybridizing to opposite strands of the nucleic acid sequence and bordering the position of the polymorphic sequence, the PCR primers being characterized as follows:
  (i) one of the third pair of PCR primers (a) being complementary at its 3'-terminal nucleotide to the second allele of the polymorphic sequence (allele B), (b) being non-complementary at its 3'-terminal nucleotide to the first allele of the polymorphic sequence (allele A), and (c) being non-complementary to the nucleic acid sequence at a single nucleotide in its 3'-terminal nucleotides 2–6; and
  (ii) one of the fourth pair of PCR primers (a) being complementary at its 3'-terminal nucleotide to the second allele of the polymorphic sequence (allele B), (b) being non-complementary at its 3'-terminal nucleotide to the first allele of the polymorphic sequence (allele A), and (c) being non-complementary to the nucleic acid sequence at one (and, preferably, two) or more nucleotides in its 3'-terminal nucleotides 2–6;

(b) carrying out the amplification reactions; and (c) detecting an amplification product as an indication of the presence, in the nucleic acid sequence, of the second allele of the polymorphic sequence (allele B).

In a related aspect, the invention features kits for carrying out the method of the invention. One particular kit for determining whether a nucleic acid sequence includes a particular allele of a polymorphic sequence includes (a) a first pair of PCR primers and a second pair of PCR primers, the first pair of PCR primers hybridizing to opposite strands of the nucleic acid sequence and bordering the position of the polymorphic sequence, and the second pair of PCR primers hybridizing to opposite strands of the nucleic acid sequence and bordering the position of the polymorphic sequence, the PCR primers being characterized as follows: (i) one of the first pair of PCR primers (a) being complementary at its 3'-terminal nucleotide to a first allele of the polymorphic sequence (allele A), (b) being non-complementary at its 3'-terminal nucleotide to a second allele of the polymorphic sequence (allele B), and (c) being non-complementary to the nucleic acid sequence at a single non-complementary nucleotide in its 3'-terminal nucleotides 2–6; and (ii) one of the second pair of PCR primers (a) being complementary at its 3'-terminal nucleotide to the first allele of the polymorphic sequence (allele A), (b) being non-complementary at its 3'-terminal nucleotide to the second allele of the polymorphic sequence (allele B), and (c) being non-complementary to the nucleic acid sequence at one (and, preferably, two) or more nucleotides in its 3'-terminal nucleotides.

If desired, the kit may also include (a) a third pair of PCR primers and a fourth pair of PCR primers, the third pair of PCR primers hybridizing to opposite strands of said nucleic acid sequence and bordering the position of the polymorphic sequence, and the fourth pair of PCR primers hybridizing to opposite strands of the nucleic acid sequence and bordering the position of the polymorphic sequence, the PCR primers being characterized as follows: (i) one of the third pair of PCR primers (a) being complementary at its 3'-terminal nucleotide to the second allele of said polymorphic sequence (allele B), (b) being non-complementary at its 3'-terminal nucleotide to the first allele of the polymorphic sequence (allele A), and (c) being non-complementary to the nucleic acid sequence at a single nucleotide in its 3'-terminal nucleotides 2–6; and (ii) one of the fourth pair of PCR primers (a) being complementary at its 3'-terminal nucleotide to the second allele of the polymorphic sequence (allele B), (b) being non-complementary at its 3'-terminal nucleotide to the first allele of the polymorphic sequence (allele A), and (c) being non-complementary to the nucleic acid sequence at one (and, preferably, two) or more nucleotides in its 3'-terminal nucleotides 2–6.

In preferred embodiments of any of the above methods or kits, the amplification reaction involving the first pair of PCR primers and the amplification reaction involving the second pair of PCR primers have different ranges of specificity; have ranges of specificity that overlap; and together have a greater than 3000-fold, and preferably at least a 10,000-fold, range of specificity.

In addition, the methods and kits are used to identify a single nucleotide polymorphism; each of the primers of the first and the second primer pairs that includes a non-complementary nucleotide in 3'-terminal nucleotides 2–6 may also include a unique hybridization tag and/or a universal primer binding site; the detection step is facilitated by the hybridization tag and/or the universal priming site; and the detection step is carried out on a solid support (for example, a chip) to which a binding partner for each hybridization tag is immobilized.

As used herein, by "polymorphic sequence" is meant any nucleotide sequence capable of variation, and by "allele" is meant one such variation. Preferably, such a variation is common in a population of organisms and is inherited in a Mendelian fashion. Such alleles may or may not have associated phenotypes. A "single nucleotide polymorphism" (or "SNP") is one type of "polymorphic sequence" which is characterized by a sequence variation of only one nucleotide.

By "range of specificity" is meant the range of nucleic acid template:PCR primer ratios at which template sequences differing by at least one nucleotide may be discriminated by assaying for the presence of detectable PCR amplification product formation.

By "hybridization tag" is meant an oligonucleotide that differs sufficiently in sequence from a target nucleic acid (for example, a target nucleic acid to be amplified) that significant cross-hybridization does not occur. When multiple hybridization tags are utilized in a single reaction mixture, these tags also preferably differ in sequence from one another such that each has a unique binding partner.

As described more fully below, the technique described herein provides a significant advance over other PCR-based techniques, particularly for carrying out genomic mapping analyses. For example, one widely used, more conventional PCR-based approach involves the use of single, short PCR primers of arbitrary sequence (called "RAPD" primers for "random amplified polymorphic DNA;" Williams et al., Nucleic Acids Research 18: 6531–6535, 1990). In a given individual, amplification with a RAPD primer typically results in the synthesis of one or more DNA fragments, while in another individual, the primer fails to amplify the same set of fragments. Because RAPD markers are dominant, they do not allow heterozygotes to be reliably scored (see Botstein et al., 1980, supra). In addition, because RAPD primers typically have low melting temperatures, the amplification of a specific sequence or sequences using such a primer is highly sensitive to PCR conditions, including template concentration and annealing temperature. It is thus often difficult to correlate results obtained by different research groups (Devos and Gale, Theor. Appl. Genet. 84: 567–572, 1992). Finally, because RAPD primers frequently amplify more than one sequence, resulting in multiple bands, analysis of the results can be complicated (Riedy et al., PCR. Nucleic Acids Research 20: 918, 1992).

Similarly, another technique in current usage exploits "AFLPs," or "amplified fragment length polymorphisms." In this method, DNAs from two polymorphic individuals are cleaved with one or two restriction endonucleases and adapters are ligated to the ends of the cleaved fragments (Vos et al., Nucleic Acids Research 23: 4407–4414, 1995). The fragments are then amplified using primers that are homologous to the adapter(s) which contain a short stretch of random nucleotides at the 3' end. These random nucleotides limit the number of amplified fragments and reveal polymorphisms between the two individuals which are detected by displaying the amplified products on an acrylamide sequencing gel. Although large numbers of AFLPs can be detected in a single lane in a sequencing gel, this technique is limited by its requirement for acrylamide gel detection, as well as by the fact that many fragments are generally amplified in each lane, resulting in a complicated pattern that requires expensive, automated high-resolution imaging technology to reliably decipher.

Finally, in yet another PCR technique, markers referred to as "simple sequence length polymorphisms" or "SSLPs" are utilized. These makers are based on amplification across tandem repeats of one or a few nucleotides known as "microsatellites." Microsatellites occur randomly in most eukaryotic genomes and display a high degree of polymorphism due to variations in the number of repeat units. Simple sequence repeats are very abundant in most mammalian genomes, and the most common simple sequence repeat is $(CA)_n$ (Dietrich et al., Proc. Natl. Acad. Sci. USA 92: 10849–10853, 1995). The repeat length varies among individuals in a species, apparently due to slippage during DNA replication (Dietrich et al., Genetics 131: 423–447, 1992). One major advantage of SSLPs is that they are co-dominant markers. That is, different patterns are obtained for organisms that are homozygous and heterozygous for the paternal alleles. Another advantage of SSLPs is that, because they are highly polymorphic at a given locus, randomly selected SSLPs are likely to be informative in any given mapping population, and are therefore especially useful for studying evolutionary relationships. However, like AFLPs, certain SSLP markers can only be assayed by acrylamide gel electrophoresis and currently available SSLP assay methods are not suited to high throughput analysis using micro DNA arrays (for example, displayed on DNA chips) (Fodor et al., Science 251: 767–773, 1991; Chee et al., Science 274: 610–614, 1996; and Southern, Trends in Genetics 12: 110–115, 1996).

In contrast to the above techniques, the presently claimed approach provides a method for mapping polymorphic alleles that combines a number of advantageous features into a single format. First, the present technique makes use of allele-specific markers that are co-dominant; this facilitates the identification of polymorphic markers in homozygotes as well as heterozygotes. In addition, the present PCR technique may be readily automated, making it a practical method for large scale mapping efforts. This automation feature stems from the fact that the technique makes use of two allele-specific primers for each particular allele having different and complementary ranges of specificity, a feature that results in an increase in the range of template DNA concentrations that may be reliably assayed. This aspect of the invention is particularly important because determinations of sample DNA concentrations need not be measured, allowing the present technique to be used in conjunction with increasingly popular solid state formats, such as DNA chip formats.

Other features and advantages of the invention will be apparent from the following detailed description, and from the claims.

BRIEF DESCRIPTION OF THE DRAWINGS

In FIG. 2A, 0.01 nanograms of template DNA are utilized, and, in FIG. 2B, 40 nanograms of template DNA are used. The relative efficiencies of amplification used for the calculations were 0.001 for primer P1 and 0.007 for primer P2 in a two primer system. P1 and P2 are specific for allele A. The closed squares represent Allele A/Primer 1; the open squares represent Allele B/Primer 1; the closed circles represent Allele A/Primer 2; and the open circles represent Allele B/Primer 2.

DETAILED DESCRIPTION

The present invention features an improved PCR amplification technique that makes use of two sets of PCR primers for each allele of a polymorphic sequence that differ in their amplification efficiencies due to the presence of differing numbers of nucleotides that are mismatched relative to the target sequence to be amplified. This improvement increases the range of specificity for the amplification step and provides a technique useful for the reliable detection of single nucleotide (allele-specific) polymorphisms. In so doing, the present approach greatly facilitates the use of allele-specific markers in the construction of genetic linkage maps, the detection of mutations or alleles in many organisms, and the sub-species typing of individuals, strains, or varieties. This invention is of particular importance because it allows total automation of the single nucleotide polymorphism detection process, for example, through the use of DNA chip technology, representing a significant advance in such detection procedures.

The present approach is now described in detail.

Allele-specific PCR Markers

Figure 1:
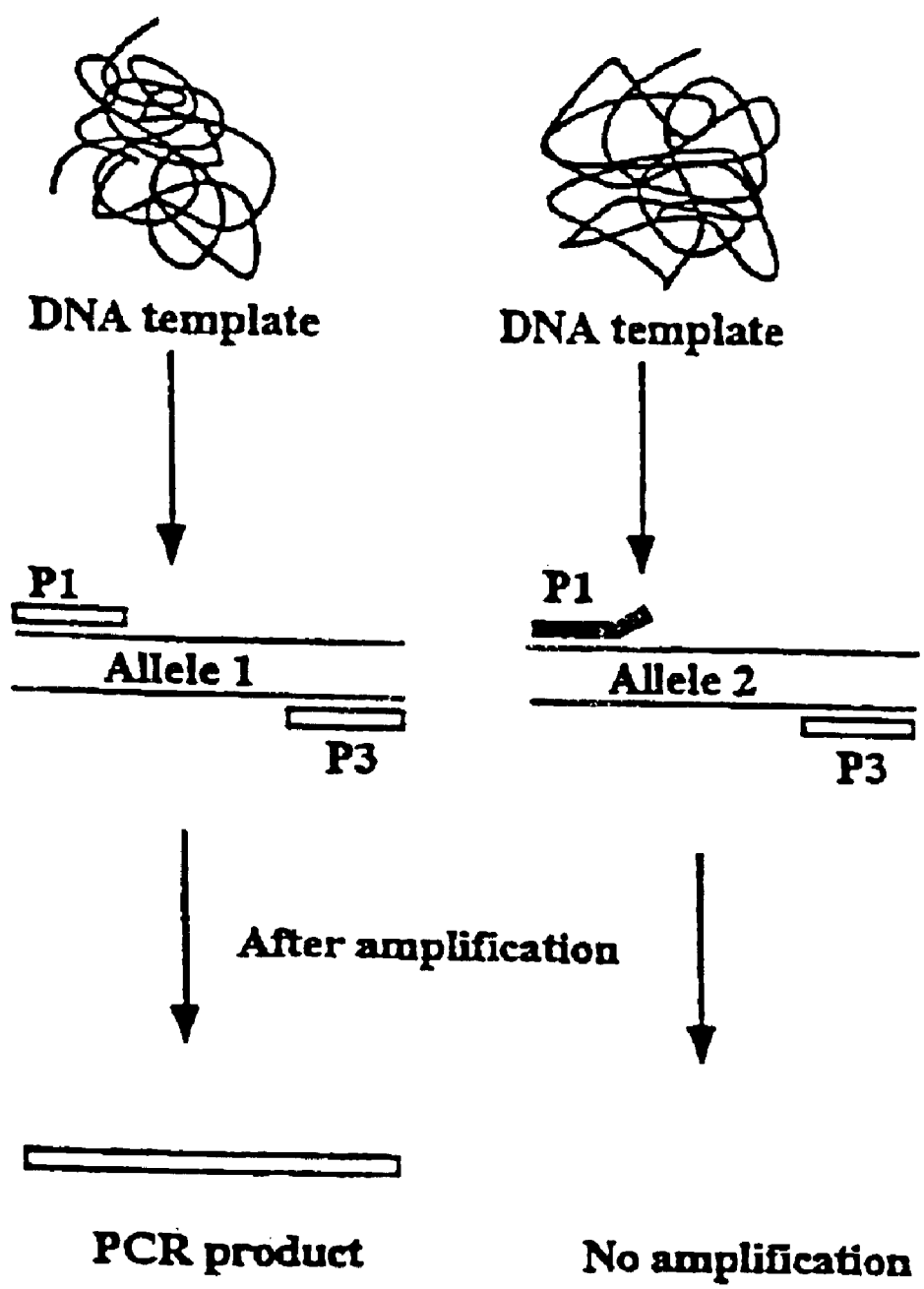
FIG. 1 is a schematic representation of the allele-specific PCR method. In this figure, primer pairs specific for allele 1 (P1 and P3) amplify allele 1, but should not (in theory) amplify allele 2. P1 forms a mismatch at the 3' end when hybridized to allele 2.

"Allele-specific PCR" is an application of PCR in which alleles that differ by one or more nucleotides can be distinguished on the basis of an amplification product (Ugozzoli and Wallace, Methods: A Companion to Methods in Enzymology 2: 42–48, 1991). As illustrated in FIG. 1, the technique utilizes primers with specific mismatches at or near the 3' end that permit preferential amplification of one allele (the target allele) relative to another (the non-target allele) (Ugozzoli and Wallace, 1991, supra; and Cha et al., PCR Methods and Applications 2: 14–20, 1992). This procedure offers the possibility of generating single nucleotide polymorphism (SNP)-based markers for the construction of linkage maps, and represents an excellent option for constructing dense maps composed entirely of these markers. Allele-specific PCR has been used previously in attempts to detect the presence or absence of one or more variant nucleotide sequences by amplification (European Patent Application No 89302331.7, Publication No 0332435), including attempts to detect point mutations associated with a variety of genetic diseases (Ugozzoli and Wallace, 1991, supra; Wenham et al., Clinical Chemistry 37: 241–244, 1991; and Chang et al., BioTechniques 22: 520–527, 1997).

Allele-specific markers are co-dominant (as long as primer pairs for specifically amplifying each of the two alleles are used), are very abundant, and are easily assayed on agarose gels. In their current usage, however, allele-specific markers have some general limitations. For example, one of the main limitations encountered in the past when using allele specific primers, and the most important obstacle for the use of these primers as markers for mapping purposes, is their relatively poor range of specificity (briefly, "range of specificity" refers to the ability of the markers to discriminate between two alleles). Relatively poor specificity represents a major problem when using these markers at high template DNA concentrations, because of the possibility of obtaining false positive results (i.e., too much amplification of the non-target allele). Previous estimates of the sensitivity of allele-specific PCR (determined by ethidium bromide staining) established that the method can reliably detect a point mutation in genomic DNA samples occurring at a frequency of approximately 1 in 40 (mutant to wild type allele ratio) (Sarkar et al., Analytical Chemistry 186: 64–68, 1990). This indicates a rather poor sensitivity and consequently inadequate levels of specificity for the ready application of this methodology to the construction of linkage maps.

In contrast, the methods of the present invention make use of two allele-specific primers for the identification of each SNP allele. These two primers have different and complementary ranges of specificity, therefore increasing the range of template DNA concentrations that may be reliably assayed. One of the primers is specific at low template DNA concentrations, and the second one shows specificity at higher concentrations of template DNA, covering in total a larger range of concentration than single allele-specific primers currently in use.

Use of Allele-specific Markers for the Construction of Linkage Maps

The allele-specific PCR procedure involves the detection of the presence or absence of one or more variant nucleotide sequences by amplification. The method relies on the presence of such nucleotide differences for the detection and analysis of genetic polymorphisms (Ugozzoli and Wallace, 1991, supra). Specific primers containing a 3'-terminal mismatch are designed to preferentially amplify one allele relative to another, as mismatched 3'-termini are PCR extended with much lower efficiencies than correctly matched termini by DNA polymerases (Petruska et al., Proc. Natl. Acad. Sci. USA 85: 6252–6256, 1988).

Although efficiency of extension may be considerably reduced during the first cycle of amplification, once extension from a mismatched primer occurs, the resultant product is fully matched with both primers, and accumulates exponentially after it is formed. Therefore, primers with mismatches at or near the 3' end are still able to extend to some degree, and a PCR product is obtained from the amplification of both alleles at the end of the amplification. The degree of specificity of the primers is therefore determined by the difference in efficiency of extension observed when amplifying target and non-target alleles with mismatched primers. Consequently, allele-specific markers will show specificity only when the product yield from the target allele exceeds the threshold of detection for the system used, and the product yield from the non-target allele does not reach that detection level.

Reductions of up to 3,000-fold in the efficiency of extension of mismatched primers compared to perfect match primers have been reported (Cha et al., 1992, supra). We calculated that for those values of relative efficiency of extension, allele-specific markers will show specificity over an approximate 2,000 to 3,000 fold range of DNA concentrations. These ranges of specificity are generally acceptable when the detection system used to score the presence or absence of the PCR product is gel electrophoresis, and the concentration of the sample has been previously determined. However, for the use of solid state technologies, such as DNA chip technology, where multiplex PCR is employed and the template DNA concentrations is unknown, those ranges of specificity may be insufficient. In multiplex PCR, different mismatched primers compete for reactants. When the efficiencies of extension of the primers used in the same reaction are not similar, differences among primers are amplified in each round of PCR, modifying individual yields and creating an imbalance in the system (Ferrie et al., American Journal of Human Genetics 51: 251–262, 1992). Under those circumstances the range of specificity of individual primers changes (Ferrie et al., 1992, supra) compromising the accuracy of the determinations. This difficulty is overcome by the present invention through an increase in the range of specificity of the markers and a resultant decrease in the possibility of error.

Broad Range PCR Amplification and its Use for Allele-specific Markers

Figure 2:
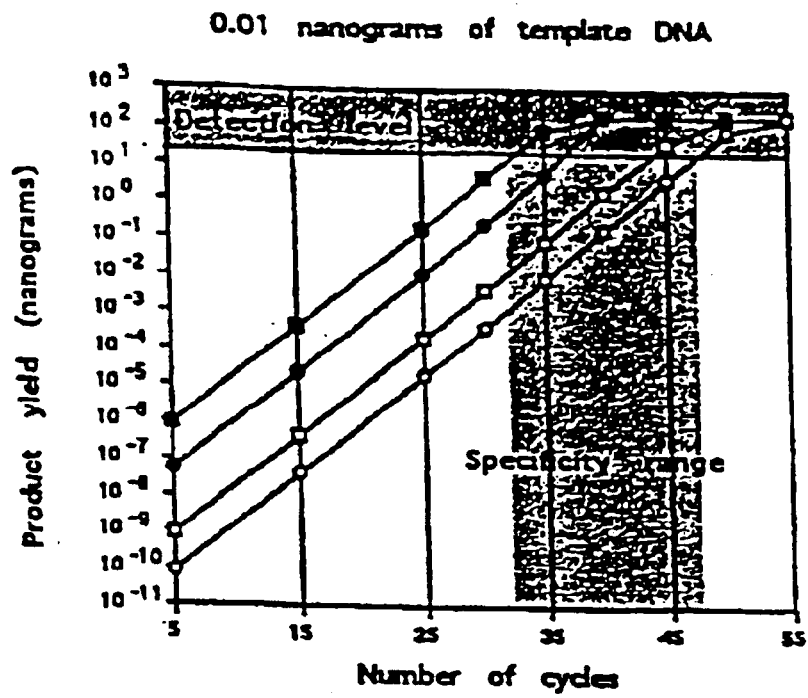
FIGS. 2A and 2B are graphs indicating the increase in product yields of alleles A (target) and B (non-target) as functions of the number of PCR cycles when using different DNA template concentrations.
Figure 2:
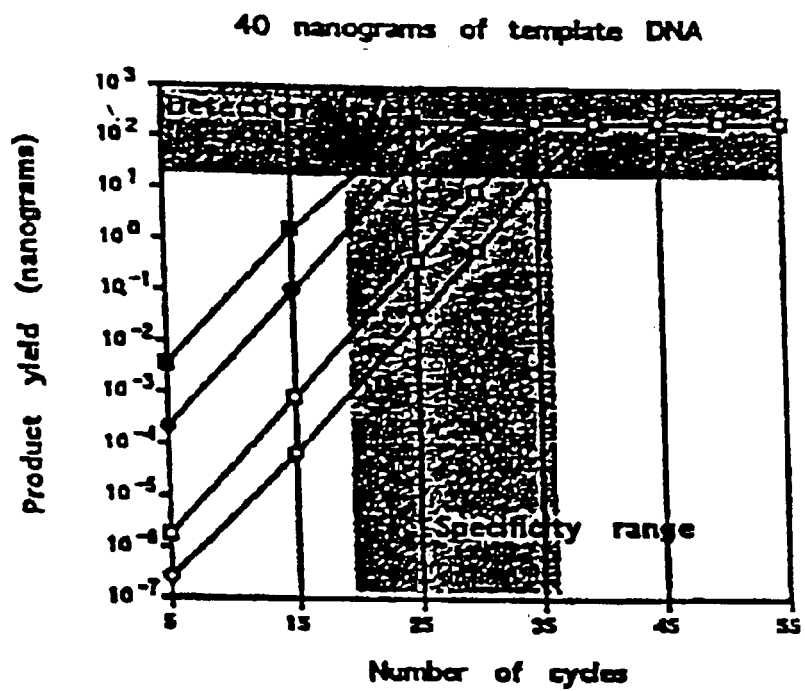

The present invention involves the use of two sets of allele-specific primers for the identification of each allele. FIG. 2 illustrates the pattern of specificity observed for two alleles, A and B, when amplified with primers P1 and P2, each of which preferentially amplifies allele A (shown in this figure is the amplification of only one allele for simplification purposes). One of the primers is specific at low template DNA concentrations (FIG. 2A), and the second one shows specificity at higher concentrations of template DNA (FIG. 2B). Moreover, the range of specificity of the two primers used to identify each one of the alleles overlaps in order to cover the entire range of DNA template concentration of the sample (FIGS. 2A and 2B).

According to the present technique, the two primers that are used to detect the same allele are designed to include one or two mismatches (but not a 3'-terminal mismatch) near the 3' end, depending on the degree of specificity that each primer should possess. Mismatch combination, location, and number of mismatches determines the efficiency with which the mismatched primers are extended. Previous studies have shown that different mismatch combinations located at the 3' end are extended with different efficiencies by Taq polymerase (Newton et al., Nucleic Acids Research 17:2503–2516, 1989; Kwok et al., Nucleic Acids Research 18:999–1005, 1990; Li et al., Proc. Natl. Acad. Sci. USA 87:4580–4584, 1990; and Sommer et al., BioTechniques 12:82–87, 1992). However, the presence of a single mismatch at the 3'-terminus of the non-target allele is sometimes insufficient to generate the desired level of discrimination with respect to the target allele, especially for mismatch combinations with efficiencies of extension that are close to the perfect match. Under these circumstances, the addition of one, and even two, additional mismatches with the non-target allele may be used to destabilize the 3'-end, providing greater differentiation with the target allele (Newton et al., 1989, supra; Cha et al., 1992, supra). For example, the addition of an extra mismatch within the last four bases of the primer may be coupled with the natural 3'-terminal mismatch to reduce PCR product yield of the non-target allele compared to the 3'-end mismatch alone (Kwok et al., 1990, supra). On the other hand, single base mismatches located either one, two, or three bases from the 3'-terminal nucleotide of the primer may be extended without significantly affecting the overall product yield of the target allele (which by definition is one that is perfectly matched with the primer at the 3'-terminus) (Kwok et al., 1990, supra).

Primers according to the present method are tailored to the particular sequence to be amplified, rather than being part of a random (for example, degenerate) oligonucleotide pool. As noted above, for any particular polymorphic sequence, the allele-specific primers for two particular alleles (A and B) of a polymorphic sequence differ at their 3' terminal nucleotides, the primer designed to detect allele A being complementary to allele A at the 3'-terminal nucleotide position and the primer designed to detect allele B being complementary to allele B at the 3'-terminal nucleotide position. The primer designed to detect allele A at low sample DNA concentration is generally designed by the addition of one introduced mismatch with respect to allele A which occurs within 6 nucleotides of the 3' end, but not at the 3'-terminal nucleotide. Since the second primer designed to detect allele A needs to be specific at higher sample DNA concentrations, two or more (typically, 2 or 3) mismatches are introduced into this second primer with respect to allele A (but again not at the 3'-terminal nucleotide) to decrease amplification efficiency of allele B to the required value. The mismatches in this second primer are positioned using the same general parameters, that is, within 6 nucleotides from the 3' end of the primer. Alternatively, the "high DNA concentration" primer for allele A may instead include only a single mismatch with allele A which causes a lower efficiency of extension than the "low DNA concentration" primer. By the above design, the two primers that detect allele A contain in addition to the "internal" mismatches described above, a 3'-terminal mismatch with allele B. For any of the above destabilizing mismatched nucleotides, the choice of a particular primer/template mismatch (i.e., A/A, T/T, C/C, G/G, A/C, C/A, A/G, G/A, T/C, C/T, T/G, or G/T) is dependent upon the mismatch combinations that are available and that which is appropriate for any given sequence context.

The length of the primers used as allele-specific primers in this invention depend on the detection method used to identify the amplification products. In the case where gel electrophoresis is used to detect amplification products, for example, the allele-specific primers are in general between 18 and 30 nucleotides in length, and preferably between 24 and 26 nucleotides (with 24 nucleotides being the most preferred).

In the case where a DNA hybridization method to a solid support is used to identify the amplification products, the allele-specific primers contain the following elements. First, the primers include a sequence proximal to the 5' end of the primer that serves as a "forward" universal primer binding site (e.g., the sequence of the phage T3 binding site for RNA polymerase). Second, in the middle of the primer, it includes a so-called unique "tag" sequence composed of approximately 20 nucleotides that does not have a corresponding sequence in the target DNA to be amplified and which serves to bind the PCR product to a solid support that contains a sequence complementary to the tag. The length of the tag sequence can be varied as required depending on the method used to detect the PCR product. And third, the primer includes a sequence proximal to its 3' end that is approximately 20–24 nucleotides and that corresponds to the sequence flanking the polymorphic sequence to be detected.

The length of the reverse primers in this invention, irrespective of the detection method, are in general between 18 and 30 nucleotides in length, and preferably between 24 and 26 nucleotides (with 24 nucleotides being the most preferred). The reverse primers used in combination with the specificity primers may be chosen from any sequence complementary to the opposite nucleic acid strand and positioned on the opposite side of the allelic marker. These reverse primers are designed using standard PCR methodologies (see, for example, *PCR Technology*, Erlich, ed., Stockton Press, London, 1989; *PCR Protocols: A Guide to Methods and Applications*, Innis et al., eds., Academic Press, Inc., New York, 1990; and Ausubel et al., *Current Protocols in Molecular Biology*, Wiley Interscience, New York, 1997).

Amplification reactions using the above primer sets are carried out by standard techniques (see references above), with the number of PCR cycles depending on the method of detection. In addition, the concentration of dNTPs may be used to modify primer specificity. For example, lower dNTP levels generally increase the stringency of the amplification (Kwok et al., A guide to the design and use of mismatched and degenerate primers, Manual Supplement, PCR Methods and Applications, S39–S47, 1994), because mismatch extension efficiency depends on the absolute concentration of the next correct nucleotide. In the experiments described herein, optimum dNTP concentration was approximately 125 mM. And the optimum values for primer concentration and $Mg^{+2}$ concentration were 7.5 pmol per reaction and 1.5 mM, respectively.

The primers used in the present methods are preferably DNA, and can be synthesized using standard techniques and, when appropriate, detectably labeled using any desired standard method (Ausubel et al., supra). In one preferred method, PCR products are labeled using universal primers. By this technique, universal primer binding sites are included, for example, in the allele-specific primers used to amplify the polymorphic sequences. The product of this initial amplification reaction is then further amplified using detectably labelled (for example, fluorescently labelled) universal primers (that are complementary to the universal primer binding sites) to generate detectably labelled amplification products. This universal primer technique is particularly useful in combination with a solid support (for example, a chip) format.

In the methods of the invention, any detectable label may be used including, but not limited to, digoxigenin, fluorescent labels (e.g., fluorescein and rhodamine), enzymes (e.g., horseradish peroxidase and alkaline phosphatase), biotin (which can be detected by anti-biotin specific antibodies or enzyme-conjugated avidin derivatives), radioactive labels (e.g., $^{32}P$ and $^{125}I$), colorimetric reagents, and chemiluminescent reagents. The labels used are detected using standard methods.

In addition, nucleic acid samples containing a polymorphic sequence to be analyzed may be obtained from any source, e.g., a tissue homogenate, fluid, or culture, and these are also prepared using standard methods.

Moreover, as mentioned above, the present method may be carried out using solid support-type formats. The solid supports useful in the invention include, but are not limited to, agarose, acrylamide, and polystyrene beads; polystyrene microtiter plates (for use in, e.g., ELISA); and nylon and nitrocellulose membranes (for use in, e.g., dot or slot blot assays). In a preferred embodiment of the invention, the solid support contains an array of nucleic acid probes. In this case, solid supports made of materials such as glass (e.g., glass plates), silicon or silicon-glass (e.g., microchips), or gold (e.g., gold plates) can be used. Methods for attaching nucleic acid probes to precise regions on such solid surfaces, e.g., photolithographic methods, are well known in the art, and can be used to make solid supports for use in the invention. Examples of such techniques are described, for example, in Schena et al., Science 270:467–470, 1995; Kozal et al., Nature Medicine 2(7):753–759, 1996; Cheng et al., Nucleic Acids Research 24(2):380–385, 1996; Lipshutz et al., BioTechniques 19(3):442–447, 1995; Pease et al., Proc. Natl. Acad. Sci. USA 91:5022–5026, 1994; Fodor et al., Nature 364:555–556, 1993; Pirrung et al., U.S. Pat. No. 5,143,854; and Fodor et al., WO 92/10092.

In practice, assaying a specific polymorphic allele may involve four separate PCR reactions (two pairs of allele-specific primers for each one of the two target and non-target alleles). Depending on the technique used to assay the PCR results, these reactions may be carried out separately (for example, if products are scored by a gel electrophoretic technique) or together (for example, if products are scored by hybridization to immobilized binding partners, such as those immobilized on a DNA chip). The actual results of the assay reflect the DNA concentration of the original template. Examples of all possible scoring alternatives are shown in Table 1. In this Table, P1/P2 preferentially amplify allele A, and P3/P4 are specific for and amplify allele B.

TABLE 1

| Template DNA Concentration | Genotype | P1 | P2 | P3 | P4 |
|---|---|---|---|---|---|
| Low | Allele A | + | − | − | − |
| Medium | Allele A | + | + | − | − |
| High | Allele A | + | + | + | − |
| Low | Allele B | − | − | + | − |
| Medium | Allele B | − | − | + | + |
| High | Allele B | + | − | + | + |
| Low | Heterozygous | + | − | + | − |
| Medium | Heterozygous | + | + | + | + |
| High | Heterozygous | + | + | + | + |

Estimation of the Range of PCR Amplification Specificity

Figure 3:
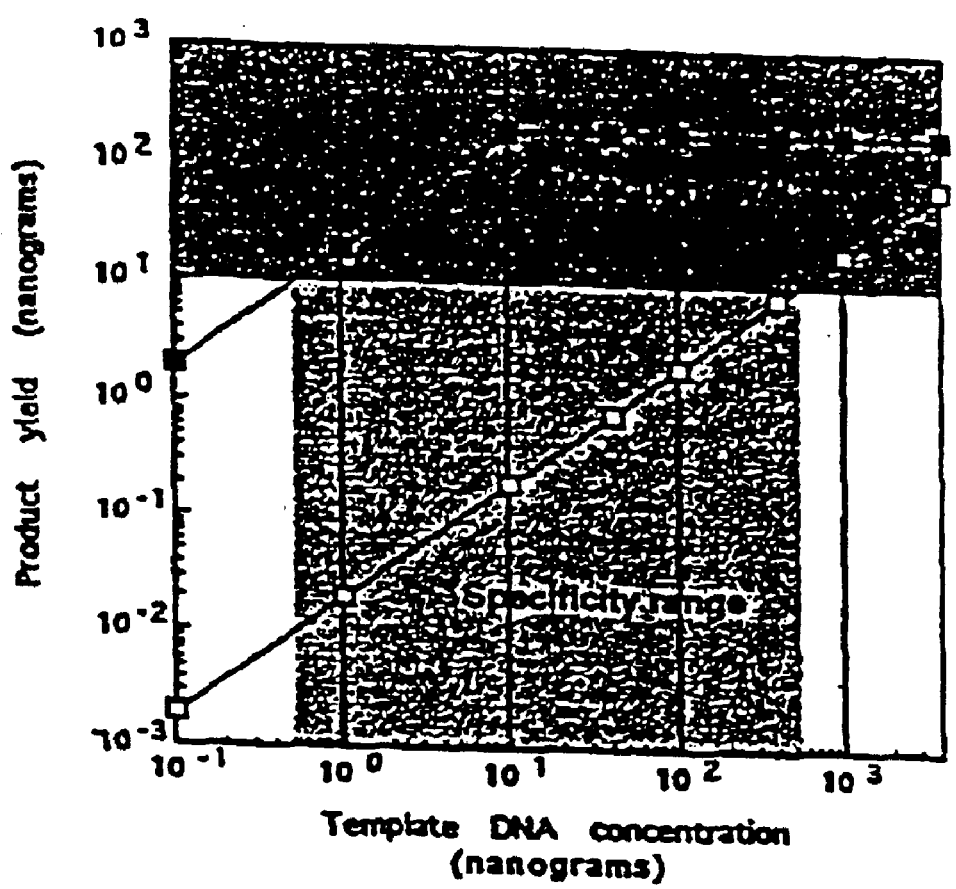
FIG. 3 is a graph illustrating the increase in product yield of target (closed squares) and non-target (open squares) as a function of DNA template concentration. Product yield was determined according to Ugozzoli and Wallace, 1991, infra.

FIG. 3 shows the range of specificity observed for a single allele-specific primer when the method of detection used is agarose gel electrophoresis. The calculations for FIG. 3 were made considering the lowest values of efficiency of extension that could be obtained on average from all different mismatch combinations. According to theoretical calculations and experimental data, we established that primers with an average relative efficiency of extension of $10^{-3}$ would maintain their specificity over an approximate 1,000 fold range of DNA concentrations.

Figure 4:
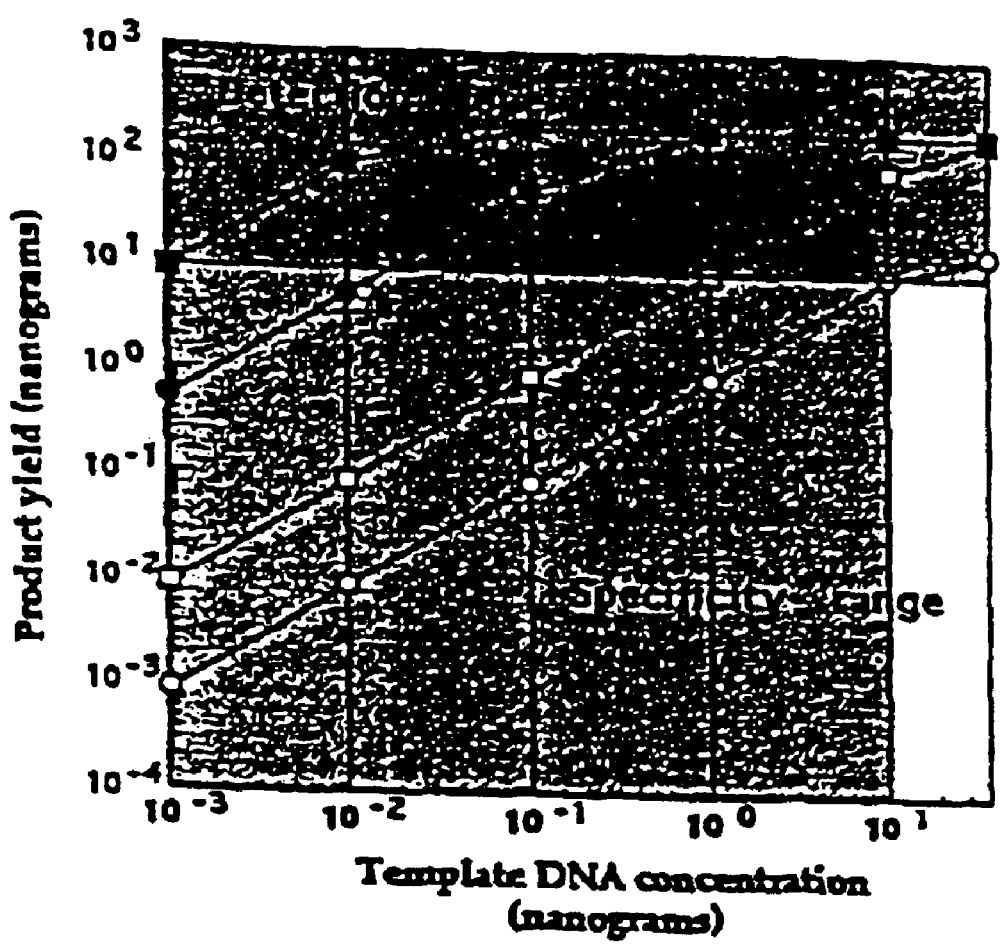
FIG. 4 is a graph illustrating the increase in product yield of allele A (target) and allele B (non-target) as a function of DNA template concentration in a two primer system. Values of product yield were calculated based on 35 cycles of amplification with primers P1 and P2 (both specific for allele A). The closed squares represent Allele A/Primer 1; the open squares represent Allele B/Primer 1; the closed circles represent Allele A/Primer 2; and the open circles represent Allele B/Primer 2.

On the other hand, FIG. 4 shows the range of specificity obtained from the use of two allele-specific primers when the method of detection is also agarose gel electrophoresis. As shown in FIG. 4 the range of specificity for the two marker system increased 10-fold compared to the method that used only one allele-specific marker (FIG. 3). This analysis indicates that the use of two allele-specific primers allows the use of allele-specific markers in those cases in which the samples analyzed show up to 10,000-fold variations in their DNA concentrations.

This increase in range of specificity is particularly useful for techniques in which DNA samples of different concentrations are utilized. For example, in fully automated DNA chip approaches, because samples are multiplexed and because it is not possible to adjust PCR conditions to take into account variations in DNA concentrations, this technique represents a significant improvement over standard methodologies.

Experimental Identification of Alleles Using Broad Range PCR Amplification

Since the range of specificity covered by the primers used to identify each one of the alleles determines the specificity of the amplification step over an appropriate range of template concentrations, range of specificity constitutes an important parameter of the present technique. As deduced from FIGS. 3 and 4, the larger the ratio between the product yields obtained from the amplification of target and non-target alleles with the mismatched primers, the larger the range of DNA concentrations within which the marker shows specificity.

In a series of experiments, we determined relative product yields between different mismatch primers and their respective perfect match primer to confirm that appropriate degrees of specificity were obtained for both primers in a set. The product yields obtained from amplification reactions using mismatch and perfect match primers were measured by standard Southern hybridization methods. The product yields obtained in all cases were quantified using a PhosphorImager (Molecular Dynamics, Sunnyvale, Calif.) after exposing the hybridized blots to PhosphorImager screens.

In these experiments, we first tested the effect of a single mismatch (in addition to the non-target 3'-terminal mismatch) on marker specificity. Forty-five single nucleotide amplified polymorphisms (or "SNAP") primers were generated with the required values of relative product yields for the markers to be assayed using agarose gel electrophoresis (some examples of the results obtained are shown in Table 2). In Table 2, the values indicate relative product yield for a variety of mismatch primers designed by using the addition of an extra mismatch at the 3'-terminus. Measurements of product yield and calculations of relative efficiencies of amplification were performed as described above. For the determination of specificity in agarose gels, a 400-fold range of template DNA concentration was used.

TABLE 2

| Primer | Specificity in agarose gels | target allele/ perfect match | non-target allele/perfect match | non target/ target allele |
|---|---|---|---|---|
| 18V2 | + | 1.2 | 0.001 | 0.0008 |
| 22V2 | + | 0.6 | 0.0002 | 0.0004 |
| 22V3 | + | 1.3 | 0.0006 | 0.0004 |
| 29V9 | + | 0.8 | 0.0008 | 0.001 |
| 29V12 | + | 0.6 | 0.0004 | 0.0007 |
| 41V11 | + | 0.7 | 0.0007 | 0.001 |
| 45V6 | + | 1.0 | 0.001 | 0.001 |
| 46V4 | + | 1.0 | 0.0009 | 0.0009 |

The values obtained from these experiments showed that the addition of an extra mismatch near the 3'-end of the primer considerably reduced PCR product yield of the non-target allele with respect to the values obtained for the 3'-end mismatch alone (Table 3 includes a few examples).

TABLE 3

| Primer | Natural mismatch alone | Addition of an extra mismatch |
|---|---|---|
| 18V2 | 0.1 | 0.001 |
| 22V2 | 0.1 | 0.0002 |
| 22V3 | 0.01 | 0.0006 |
| 29V9 | 0.01 | 0.0008 |

In some cases, values of relative product yield of up to $10^{-4}$ were obtained for the amplification of non-target alleles relative to perfect match primers (Primers 22V2, 22V3, 29V9, 29V12, 41V11, 46V4; Table 2). On the other hand, the presence of a single mismatch 2 or 3 bases from the 3' end did not have a significant effect at reducing the overall product yield of the target allele (Table 2). These experiments indicated that the relative efficiencies of extension between target and non-target alleles were reliably increased by primer design. Finally, we made designs for all 12 possible natural mismatch combinations that could be present in the SNP sequences, and, in all cases, reliably obtained the desired ranges of specificity for these primers (not shown).

Also, as shown in Table 2, the lowest value of relative product yield obtained from non-target alleles (compared to perfect match) was $2 \times 10^{-4}$ when amplified with primers containing one extra mismatch near the 3' end (Primer 22V2). This implied that the relative product yield obtained for the target alleles would have to be higher than 0.1 (with respect to the perfect match) in order to maintain the required $10^{-3}$ range of specificity. The use of primer combinations that decreased product yield of the target allele below values of 0.1 would only decrease specificity, since no further reduction on the product yield of non-target alleles would be obtained from the addition of such mismatch combinations.

In addition, in these experiments, other primers containing two extra mismatches (in addition to the 3'-terminal non-target mismatch) were tested for their ability to increase marker specificity. These results are shown in Table 4. In this Table, the values indicate the relative product yield of non-target and target alleles (compared to perfect match) obtained after amplification with primers containing two additional mismatches near the 3'-terminus.

TABLE 4

| Mismatch combination | Non-target allele/perfect match | Target allele/perfect match |
| --- | --- | --- |
| 39V16 | 0.00003 | 0.01 |
| 18V14 | 0.00007 | 0.06 |
| 49V16 | 0.00009 | 0.003 |
| 49V12 | 0.00007 | 0.001 |
| 29v14 | 0.00004 | 0.01 |
| 29v17 | 0.00003 | 0.04 |
| 25v131 | 0.00006 | 0.09 |

As shown in Table 4, relative product yields for non-target alleles of up to $2.3 \times 10^{-5}$ (compared to the perfect match) were obtained when two additional mismatches were introduced to design the primers, indicating that specificity over higher ranges of DNA concentrations were obtained.

In addition, in a parallel set of experiments, two primers with complementary ranges of specificity were generated by the introduction of one and two mismatches, respectively, near the 3' end, according to the required level of discrimination needed. In parallel reactions, PCR amplification was carried out using "perfect match" primers that contained sequences identical to those described above, but lacking the mismatched nucleotides. Table 5 shows the values of relative product yield obtained from the amplification of these allele-specific primers (values of product yield are relative to those obtained with perfect match primers). In this Table, "one extra mismatch" and "two extra mismatches" refers to the number of non-complementary nucleotides present in the primer, in addition to the 3'-terminal mismatch of the primer with respect to the non-target allele.

TABLE 5

| | One extra mismatch | | Two extra mismatches | |
| --- | --- | --- | --- | --- |
| Mismatch combination | Target allele/perfect match | Non-target allele/perfect match | Target allele/perfect match | Non-target allele/perfect match |
| A:C | 1.2 | 0.001 | 0.06 | 0.00007 |
| G:T | 0.8 | 0.0008 | 0.08 | 0.00004 |
| C:C | 0.8 | 0.0008 | 0.01 | 0.00004 |
| G:G | 0.6 | 0.0004 | 0.04 | 0.00002 |

As shown in Table 5, the addition of one extra mismatch (in addition to the 3'-terminal non-target mismatch) at the 3' end resulted in a difference in relative product yield between target and non-target alleles of approximately 1,000-fold (Table 5). In addition, the relative product yield of the target allele compared to the perfect match in these particular cases was relatively high (Table 5), allowing the marker to be specific under conditions of low sample concentration (FIG. 2A, FIG. 4).

The addition of two extra mismatches (in addition to the 3'-terminal non-target mismatch) near the 3' end decreased the product yield of non-target alleles to average levels of $10^{-5}$ compared to perfect match primers, making the markers specific at high sample DNA concentrations (Table 5, FIG. 2B, and FIG. 4). In all cases, ratios between product yield of the target allele amplified with the primer containing one extra mismatch and the non-target allele amplified with the primer containing two extra mismatches (extremes of the range) was at least $10^4$ fold, a value that guarantees specificity over a 10,000-fold range of DNA concentrations (FIG. 4). Finally, as shown in Table 5, relative amplification efficiencies for the complementary primers overlapped in all cases, ensuring specificity over the entire range of DNA concentrations. These results indicated the feasibility of generating markers with ranges of specificity adequately high to cover large ranges of DNA concentration (approximately a 10,000-fold range).

Figure 5:
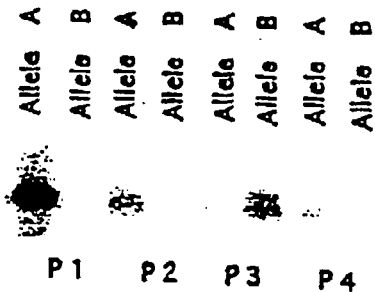
FIG. 5 is series of photographs and graphs illustrating the hybridization pattern of alleles A and B amplified with allele-specific primers P1/P2 (specific for allele A) and P3/P4 (specific for allele B).
Figure 5:
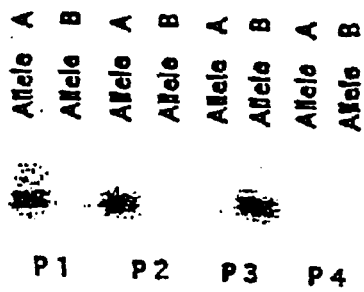
Figure 5:
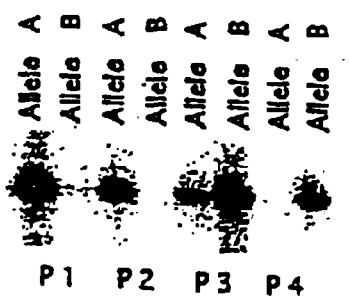

In a final experiment the reliability of the method was tested by hybridization of the products amplified from two alleles, A and B, with allele-specific primers P1/P2 (specific for allele A), and P3/P4 (specific for allele B), holding the primer concentrations constant and using different concentrations of template DNA (ranging from 0.01 to 10 nanograms of DNA). FIG. 5 shows that, at low template DNA concentration (0.01 nanograms), primers P1 and P3 showed specificity for their respective alleles (A and B). At higher DNA concentrations (10 nanograms), in the case of allele B, primer P3 lost specificity, but primer P4 retained specificity. These results demonstrated the feasibility of the use of the two primer system in the construction of linkage maps in those cases where DNA concentrations vary over a 10,000-fold range.

Chip Based Approaches

Chip-based approaches, involving microarrays of DNA sequences as gene-specific hybridization targets, have been developed recently for the detection of single-nucleotide polymorphisms and for the quantitative measurement of expression of genes in plants and humans (Schena et al., Science 270: 467–470, 1995; and Schena et al., Proc. Natl. Acad. Sci. USA 93: 10614–10619, 1996). The power of DNA chip technology for genome analysis resides in the large number of probes that can be tested using a single chip. The potential applications of this new technology are vast, and include use in mapping procedures. Although single-nucleotide polymorphisms are quite adaptable to chip-based assays (Jordan and Collins, Nature 380: 111–112, 1996), implementation of totally automated mapping systems using such markers has sometimes been problematic due to the lack of a robust methodology, particularly for monitoring single nucleotide polymorphisms (Jordan and Collins, 1996, supra). In theory SNPs can be assayed directly on high density Affymetrix chips using so-called tiling procedures; however, these methods have generally not been sufficiently reproducible or sensitive to reliably assay most SNPs.

In contrast, the present technique is ideally suited to DNA chip applications. In particular, the capability of two (or more) sets of primers to maintain allele specificity within a broad range of DNA concentrations allows the use of allele-specific markers in this format, since reactions may be carried out without a requirement for previous determinations of sample DNA concentrations. By exploiting a combination of two allele-specific PCR primers with complementary ranges of specificity, a considerable increase is obtained in the overall range of DNA concentrations that may be reliably assayed compared to values obtained with single-allele specific primers.

Figure 6:
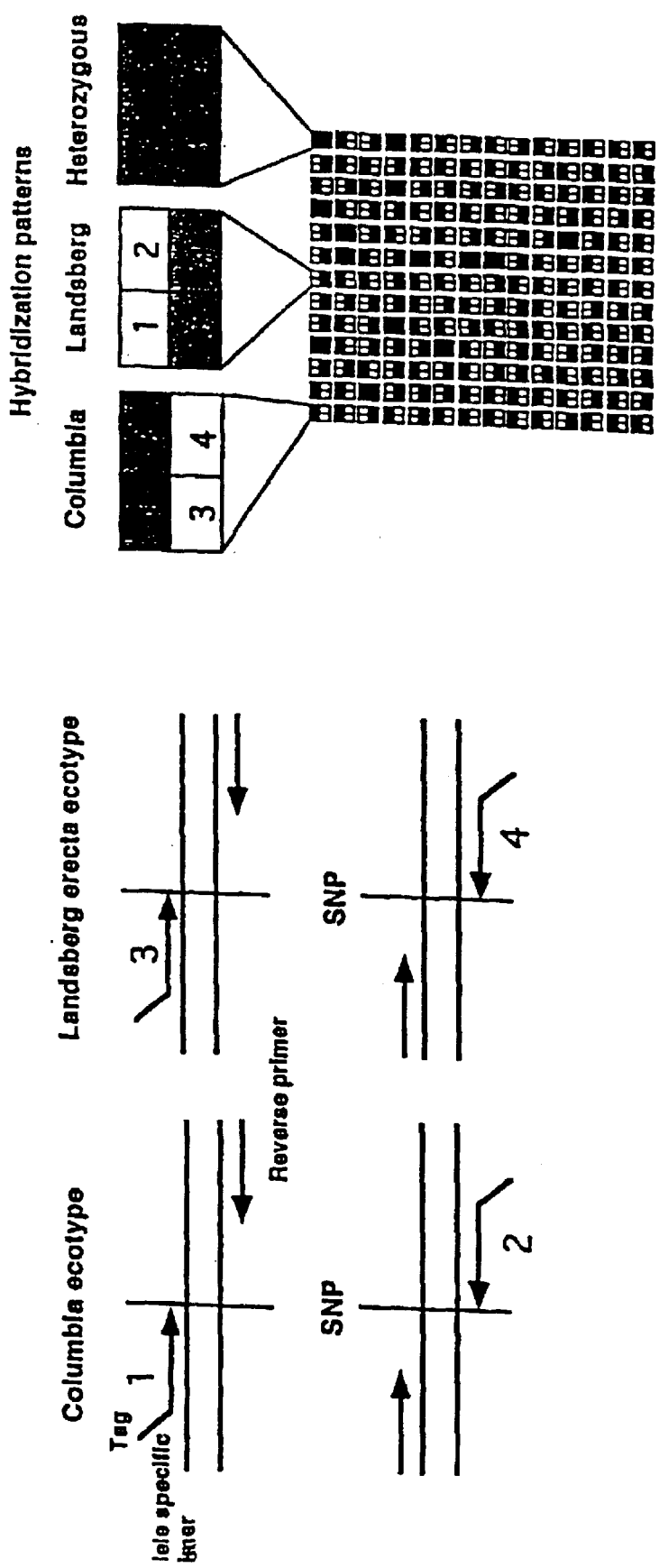
FIG. 6 is a schematic representation of the use of the present method in a DNA chip format.

As shown in FIG. 6, the present technique facilitates the detection of allele-specific amplification products. In this figure, primers P1 and P2 are specific for the allele associated with *Arabidopsis thaliana* ecotype Columbia, and primers P3 and P4 are specific for Arabidopsis ecotype Landsberg erecta. P1 differs from P2, and P3 differs from P4, in the number of mismatches with the target sequence near the 3' end, resulting in primers having different but overlapping ranges of specificity. In addition, these primers each contain a multiplex oligonucleotide tag (a hybridization tag) that differs in sequence from the primer itself as well as the target sequence. Following amplification, the labelled PCR products (for example, radioactive or fluorescent PCR products) are scored using DNA chips on which are immobilized (in discrete quadrants) binding partners for each of the multiplex tags. By carrying out hybridization to these tags, the presence of the allelic marker is determined, as well as a determination of whether the sample DNA was homozygous or heterozygous at that allele.

Any number of allelic markers may be simultaneously tested in this manner simply by including primer sets for each target marker in the PCR amplification reaction mixture, and assaying by hybridization to binding partners for each of those markers, for example, using unique multiplex tags immobilized on a solid support.

Other Embodiments

The broad range PCR techniques described herein may be used in any appropriate context, although mapping represents a particularly useful application of the method. In addition, such mapping approaches find use in any number of organisms (including plants and animals) and are most useful for organisms having incomplete genomic sequence information.

Other embodiments are within the claims.

What is claimed is:

1. A method for determining whether a nucleic acid sequence comprises a particular allele of a polymorphic sequence, said method comprising:

(a) contacting said nucleic acid sequence, in one amplification reaction or separate amplification reactions, with a first pair of PCR primers and a second pair of PCR primers under conditions that allow hybridization of said PCR primers to said nucleic acid sequence, a first member of said first pair of PCR primers hybridizing to one strand of said nucleic acid sequence and the other member of said first pair of PCR primers hybridizing to the other strand of said nucleic acid sequence on the opposite side of said polymorphic sequence from the side to which said first member of said first pair hybridizes, and a first member of said second pair of PCR primers hybridizing to one strand of said nucleic acid sequence and the other member of said second pair of PCR primers hybridizing to the other strand of said nucleic acid sequence on the opposite side of said polymorphic sequence from the side to which said first member of said second pair hybridizes, said PCR primers being characterized as follows:

(i) one of said first pair of PCR primers is (a) complementary at its 3'-terminal nucleotide to a first allele of said polymorphic sequence, (b) non-complementary at its 3'-terminal nucleotide to a second allele of said polymorphic sequence, and (c) non-complementary to said nucleic acid sequence at a single nucleotide that is disposed within the five nucleotides adjacent to said 3'-terminal nucleotide, wherein said first pair of primers is capable of amplifying said first allele under appropriate conditions; and (ii) one of said second pair of PCR primers is (a) complementary at its 3'-terminal nucleotide to said first allele of said polymorphic sequence, (b) non-complementary at its 3'-terminal nucleotide to said second allele of said polymorphic sequence, and (c) non-complementary to said nucleic acid sequence at one or more nucleotides that are disposed within the five nucleotides adjacent to said 3'-terminal nucleotide, wherein said second pair of primers is capable of amplifying said first allele under appropriate conditions;

(b) carrying out said amplification reaction or reactions, wherein the amplification reaction involving said first pair of PCR primers and the amplification reaction involving said second pair of PCR primers have different ranges of specificity; and (c) detecting any amplification product of step (b), wherein the presence of amplification product is indicative of the presence of said first allele in said nucleic acid sequence.

2. The method of claim 1, wherein said ranges of specificity overlap.

3. The method of claim 2, wherein said amplification reaction involving said first pair of PCR primers and said amplification reaction involving said second pair of PCR primers together have a greater than 3000-fold range of specificity.

4. The method of claim 3, wherein said amplification reaction involving said first pair of PCR primers and said amplification reaction involving said second pair of PCR primers together have at least a 10,000-fold range of specificity.

5. The method of claim 1, wherein said one of said second pair of PCR primers in step (a)(ii) includes at least two non-complementary nucleotides that are disposed within the five nucleotides adjacent to the 3'-terminal nucleotide of each primer.

6. The method of claim 1, wherein said polymorphic sequence comprises a single nucleotide polymorphism.

7. The method of claim 1, wherein said one of said first pair of PCR primers in step (a)(i) and said one of said second pair of PCR primers in step (a)(ii) also comprise a universal primer binding site.

8. The method of claim 7, wherein said detecting step comprises amplification of said product of step (b) using a detectably labelled PCR primer that hybridizes to said universal primer binding site.

9. The method of claim 1, wherein said one of said first pair of PCR primers in step (a)(i) and said one of said second pair of PCR primers in step (a)(ii) also comprise a unique hybridization tag.

10. The method of claim 9, wherein said detection step is carried out on a solid support to which a binding partner for each hybridization tag is immobilized.

11. The method of claim 10, wherein said solid support is a chip.

12. The method of claim 1, further comprising:

(d) contacting said nucleic acid sequence, in one amplification reaction or separate amplification reactions, with a third pair of PCR primers and a fourth pair of PCR primers under conditions that allow hybridization of said PCR primers to said nucleic acid sequence, a first member of said third pair of PCR primers hybridizing to one strand of said nucleic acid sequence and the other member of said third pair of PCR primers hybridizing to the other strand of said nucleic acid sequence on the opposite side of said polymorphic sequence from the side to which said first member of said third pair hybridizes, and a first member of said fourth pair of PCR primers hybridizing to one strand of said nucleic acid sequence and the other member of said fourth pair of PCR primers hybridizing to the other strand of said nucleic acid sequence on the opposite side of said polymorphic sequence from the side to which said first member of said fourth pair hybridizes, said PCR primers being characterized as follows:

(i) one of said third pair of PCR primers is (a) complementary at its 3'-terminal nucleotide to said second allele of said polymorphic sequence, (b) non-complementary at its 3'-terminal nucleotide to said first allele of said polymorphic sequence, and (c) non-complementary to said nucleic acid sequence at a single nucleotide that is disposed within the five nucleotides adjacent to said 3'-terminal nucleotide, wherein said third pair of primers is capable of amplifying said second allele under appropriate conditions; and (ii) one of said fourth pair of PCR primers is (a) complementary at its 3'-terminal nucleotide to said second allele of said polymorphic sequence, (b) non-complementary at its 3'-terminal nucleotide to said first allele of said polymorphic sequence, and (c) non-complementary to said nucleic acid sequence at one or more nucleotides that are disposed within the five nucleotides adjacent to said 3'-terminal nucleotide, wherein said fourth pair of primers is capable of amplifying said second allele under appropriate conditions; and (e) carrying out said amplification reaction or reactions; and (f) detecting any amplification product of step (e), wherein the presence of amplification product is indicative of the presence of said second allele in said nucleic acid sequence.

13. A kit for determining whether a nucleic acid sequence comprises a particular allele of a polymorphic sequence, said kit comprising:

(a) a first pair of PCR primers and a second pair of PCR primers, a first member of said first pair of PCR primers hybridizing to one strand of said nucleic acid sequence and the other member of said first pair of PCR primers hybridizing to the other strand of said nucleic acid sequence on the opposite side of said polymorphic sequence from the side to which said first member of said first pair hybridizes, and a first member of said second pair of PCR primers hybridizing to one strand of said nucleic acid sequence and the other member of said second pair of PCR primers hybridizing to the other strand of said nucleic acid sequence on the opposite side of said polymorphic sequence from the side to which said first member of said second pair hybridizes, wherein said PCR primers are characterized as follows:

(i) one of said first pair of PCR primers is (a) complementary at its 3'-terminal nucleotide to a first allele of said polymorphic sequence, (b) non-complementary at its 3'-terminal nucleotide to a second allele of said polymorphic sequence, and (c) non-complementary to said nucleic acid sequence at a single nucleotide that is disposed within the five nucleotides adjacent to said 3'-terminal nucleotide, wherein said first pair of primers is capable of amplifying said first allele under appropriate conditions; and (ii) one of said second pair of PCR primers is (a) complementary at its 3'-terminal nucleotide to said first allele of said polymorphic sequence, (b) non-complementary at its 3'-terminal nucleotide to said second allele of said polymorphic sequence, and (c) non-complementary to said nucleic acid sequence at one or more nucleotides that are disposed within the five nucleotides adjacent to said 3'-terminal nucleotide, wherein said second pair of primers is capable of amplifying said first allele under appropriate conditions, wherein an amplification reaction involving said first pair of PCR primers and an amplification reaction involving said second pair of PCR primers have different ranges of specificity.

14. The kit of claim 13, further comprising:

(b) a third pair of PCR primers and a fourth pair of PCR primers, a first member of said third pair of PCR primers hybridizing to one strand of said nucleic acid sequence and the other member of said third pair of PCR primers hybridizing to the other strand of said nucleic acid sequence on the opposite side of said polymorphic sequence from the side to which said first member of said third pair hybridizes, and a first member of said fourth pair of PCR primers hybridizing to one strand of said nucleic acid sequence and the other member of said fourth pair of PCR primers hybridizing to the other strand of said nucleic acid sequence on the opposite side of said polymorphic sequence from the side to which said first member of said fourth pair hybridizes, wherein said PCR primers are characterized as follows:

(i) one of said third pair of PCR primers is (a) complementary at its 3'-terminal nucleotide to said second allele of said polymorphic sequence, (b) non-complementary at its 3'-terminal nucleotide to said first allele of said polymorphic sequence, and (c) non-complementary to said nucleic acid sequence at a single nucleotide that is disposed within the five nucleotides adjacent to said 3'-terminal nucleotide, wherein said third pair of primers is capable of amplifying said second allele under appropriate conditions; and (ii) one of said fourth pair of PCR primers is (a) complementary at its 3'-terminal nucleotide to said second allele of said polymorphic sequence, (b) non-complementary at its 3'-terminal nucleotide to said first allele of said polymorphic sequence, and (c) non-complementary to said nucleic acid sequence at one or more nucleotides that is disposed within the five nucleotides adjacent to said 3'-terminal nucleotide, wherein said fourth pair of primers is capable of amplifying said second allele under appropriate conditions.

15. The kit of claim 13, wherein said one of said first pair of PCR primers in step (a)(i) and said one of said second pair of PCR primers in step (a)(ii) also comprise a universal primer binding sequence.

16. The kit of claim 13, wherein said one of said first pair of PCR primers in step (a)(i) and said one of said second pair of PCR primers in step (a)(ii) also comprise a unique hybridization tag.

17. The kit of claim 16, wherein said kit further includes a solid support to which is immobilized a binding partner for each hybridization tag.

18. The kit of claim 17, wherein said solid support is a chip.

* * * * *